United States Patent
Kim et al.

(10) Patent No.: US 11,021,432 B2
(45) Date of Patent: Jun. 1, 2021

(54) SYSTEM FOR CONTINUOUSLY PURIFYING REACTION PRODUCT OF ESTERIFICATION

(71) Applicant: LG CHEM, LTD., Seoul (KR)

(72) Inventors: Hyun Kyu Kim, Daejeon (KR); Sung Kyu Lee, Daejeon (KR); Hyoung Jun, Daejeon (KR); Chan Hyu Jin, Daejeon (KR); Jeong Ju Moon, Daejeon (KR); Joo Ho Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 16/838,816

(22) Filed: Apr. 2, 2020

(65) Prior Publication Data

US 2020/0317601 A1    Oct. 8, 2020

(30) Foreign Application Priority Data

Apr. 4, 2019 (KR) .................. 10-2019-0039718
Mar. 30, 2020 (KR) .................. 10 2020-0038460

(51) Int. Cl.
*C07C 67/54* (2006.01)
*B01J 19/00* (2006.01)
(Continued)

(52) U.S. Cl.
CPC .............. *C07C 67/54* (2013.01); *B01D 3/38* (2013.01); *B01D 19/001* (2013.01); *B01J 8/04* (2013.01); *B01J 19/00* (2013.01); *C07C 67/62* (2013.01)

(58) Field of Classification Search
CPC ......... C07C 67/02; C07C 67/08; C07C 67/54; C07C 67/62; B01D 3/06; B01D 3/14;
(Continued)

(56) References Cited

U.S. PATENT DOCUMENTS 2,955,989 A * 10/1960 Dimler, Jr. .............. C07C 67/54
  203/6
4,241,216 A * 12/1980 Bergman ................ C07C 67/08
  560/191

(Continued)

FOREIGN PATENT DOCUMENTS

JP   2010-095467 A   4/2010
JP   2013-193998 A   9/2013
(Continued)

OTHER PUBLICATIONS

KR101663586, Kim Jeong Gon et al, Dioctyl terephthalate manufacturing method increased reaction conversion rate through unique reaction temperature control., English translation, 15 pages (Year: 2016).*

(Continued)

*Primary Examiner* — Yate' K Cutliff
(74) *Attorney, Agent, or Firm* — Dentons US LLP (57) ABSTRACT

The present disclosure relates to a system and a method for continuously purifying a reaction product of esterification, where the system includes a neutralizer, a distiller, and a product purifier. Through the present system and the method, it is possible to perform a continuous purification process efficiently, and to reduce lower alcohol wastewater generated during purification.

14 Claims, 3 Drawing Sheets

(51) Int. Cl.
    *C07C 67/62*     (2006.01)
    *B01D 3/38*     (2006.01)
    *B01J 8/04*     (2006.01)
    *B01D 19/00*     (2006.01)

(58) Field of Classification Search
    CPC . B01D 3/38; B01D 3/40; B01D 19/001; B01J 8/04
    See application file for complete search history.

(56) References Cited

U.S. PATENT DOCUMENTS

| 2007/0277430 | A1* | 12/2007 | Jackman | C11C 3/003 |
| | | | | 44/308 |
| 2017/0015810 | A1* | 1/2017 | Miyazaki | C08K 5/12 |
| 2019/0263745 | A1* | 8/2019 | Lee | C07C 67/03 |

FOREIGN PATENT DOCUMENTS

| JP | 2015-140336 A | 8/2015 | |
| KR | 10-2013-0042743 A | 4/2013 | |
| KR | 10-1663586 B1 | 10/2016 | |
| KR | 101663586 * | 10/2016 | .......... B01J 31/0209 |
| KR | 10-2019-0027623 A1 | 3/2019 | |
| WO | 2007-074750 A1 | 6/2009 | |

OTHER PUBLICATIONS

Nadeem Rezaq Janjua et al., "Systemic Uptake of Diethyl Phthalate, Dibutyl Phthalate, and Butyl Paraben Following Whole-Body Topical Application and Reproductive and Thyroid Hormone Levels in Humans", Environmental Science and Technology, 2007, 41, pp. 5564-5570.

Mustafizur Rahman et al., "The plasticizer market: an assessment of traditional plasticizers and research trends to meet new challenges", Progress in Polymer Science, 2004, 29, pp. 1223-1248.

* cited by examiner

SYSTEM FOR CONTINUOUSLY PURIFYING REACTION PRODUCT OF ESTERIFICATION

CROSS-REFERENCE TO RELATED APPLICATIONS

This application claims the benefit of and priority to Korean Application No. 10-2019-0039718, filed on Apr. 4, 2019, and Korean Application No. 10-2020-0038460, filed on Mar. 30, 2020, all of which are hereby incorporated by reference in their entirety for all purposes as if fully set forth herein.

TECHNICAL FIELD

The present invention relates to a system for continuously purifying a reaction product of esterification.

BACKGROUND ART

Phthalate-based plasticizers had occupied 92% of the world's plasticizer market by the 20th century (Mustafizur Rahman and Christopher S. Brazel "The plasticizer market: an assessment of traditional plasticizers and research trends to meet new challenges" Progress in Polymer Science 2004, 29, 1223-1248), and are additives used to improve the processability of polyvinyl chloride (hereinafter, referred to as PVC) by imparting flexibility, durability, cold resistance, and the like and lowering viscosity during melting. Phthalate-based plasticizers are introduced into PVC in various contents and used not only for hard products such as rigid pipes, but also for soft products such as food packaging materials, blood bags, and flooring materials since the phthalate-based plasticizers are soft and stretchable. Thus, the phthalate-based plasticizers are more closely related to real life than any other materials and are widely used for materials which come into direct contact with a human body.

However, despite the compatibility with PVC and excellent softness imparting properties of phthalate-based plasticizers, there has been controversy over the harmful nature of the phthalate-based plasticizers in that when a PVC product containing a phthalate-based plasticizer is used in real life, the phthalate-based plasticizer may be leaked little by little out of the product and act as a suspected endocrine disruptor (environmental hormone) and a carcinogen to the level of a heavy metal (NR Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570). Particularly, since a report was published in the 1960s in the United States that diethylhexyl phthalate (di-(2-ethylhexyl) phthalate, DEHP), the most used phthalate plasticizer, leaked out of PVC products, global environmental regulations have started to be implemented in addition to various studies on the harmful nature of the phthalate-based plasticizer on human bodies, boosted by increasing interest in environmental hormones in the 1990s.

Thus, in order to respond to environmental hormonal problems and environmental regulations due to the leakage of phthalate-based plasticizers, many researchers have been conducting research in order to develop a new non-phthalate-based alternative plasticizer without phthalic anhydride used in the manufacturing of phthalate-based plasticizers, or to develop a leakage suppression technology which suppresses the leakage of phthalate-based plasticizers, thereby significantly reducing risks to human bodies and which meets environmental standards.

Meanwhile, as non-phthalate-based plasticizers, terephthalate-based plasticizers not only have an equivalent level of physical properties with phthalate-based plasticizers, but also have been spotlighted as a material free from environmental problems, so that various types of terephthalate-based plasticizers have been developed. In addition, research on developing terephthalate-based plasticizers with excellent physical properties as well as research on equipment for manufacturing such terephthalate-based plasticizers have been actively conducted, and there has been a demand for more efficient, more economical and simpler process designs in terms of process design.

There has also been a constant demand for improving a process for manufacturing such terephthalate plasticizers in terms of various aspects, such as product productivity, separation efficiency of a purification process, the purity of a product, wastewater treatment by azeotropic distillation, and energy loss.

Prior Art Document (Patent Document 1) Korean Patent Laid-Open Publication No. 10-2013-0042743
(Non-patent Document 1) Mustafizur Rahman and Christopher S. Brazel "The plasticizer market: an assessment of traditional plasticizers and research trends to meet new challenges" Progress in Polymer Science 2004, 29, 1223-1248
(Non-patent Document 2) N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570

DISCLOSURE OF THE INVENTION

Technical Problem

The present invention relates to a system capable of continuously purifying an unpurified product mixture produced from an esterification reaction and a continuous purification process using the same. An aspect of the present invention provides a system for purifying a reaction product of esterification and a method for purifying the same, in which the amount of wastewater of lower alcohol is reduced and the lower alcohol contained in the wastewater may be continuously and efficiently separated.

Technical Solution

According to an aspect of the present invention, there is provided a system for continuously purifying a reaction product of esterification, wherein the system includes a neutralizer including an inlet into which an unpurified product mixture containing a mixture of two kinds of alcohols having different esters and different numbers of carbon atoms is injected, a neutralization agent injection port through which a basic aqueous solution is injected as a neutralization agent, an inner space in which neutralization and water separation are performed, a first discharge port from which an organic layer fraction is discharged, and a second discharge port from which a water layer fraction is discharged, a distiller including an organic layer fraction injection port connected to the first discharge port of the neutralizer, a separation space in which the separation of the alcohol mixture is performed, an alcohol-rich stream discharge port provided on an upper portion of the separation space, and an ester-rich stream discharge port provided on a lower portion of the separation space, and a product purifier including a purifier inlet connected to the ester-rich stream discharge port of the distiller, a purification space in which gas-liquid separation is performed, an alcohol discharge port provided on an upper portion of the purification space and from which an alcohol fraction is discharged, and a product discharge port provided on a lower portion of the purification space and from which an ester fraction is discharged, wherein the inner space of the neutralizer is provided with one or more partition walls such that the inner space is divided into a neutralization space and a layer separation space in the left and right directions respectively and a passage connecting the two spaces is formed, and the passage starts from an upper portion of the neutralization space.

According to another aspect of the present invention, there is provided a method for continuously purifying a reaction product of esterification, the method which may be implemented through the above continuous purification system, wherein the method specifically includes a step S1 of performing layer separation on an unpurified product mixture including an alcohol mixture, as an unreacted material, containing two kinds of alcohol having different numbers of carbon atoms selected from 3 to 10 carbon atoms and including ester which is a product of an esterification reaction into an organic layer fraction which is rich in ester and a water layer fraction including lower alcohol in the presence of a basic aqueous solution in a neutralizer having a partition wall structure, a step S2 of injecting the organic layer fraction into a distiller to remove an alcohol-rich stream from an upper portion of the distiller and to discharge an ester-rich stream from a lower portion thereof, and a step S3 of injecting the ester-rich stream into a product purifier to separate an ester fraction from a lower portion of the product purifier and to separate an alcohol fraction from an upper portion thereof.

According to exemplary embodiments described in the present invention, a purification system and a purification method may be provided in which the amount of wastewater containing lower alcohol is reduced and the lower alcohol included in the wastewater is efficiently separated in purifying a product of an esterification reaction and the process may be continuously performed.

BRIEF DESCRIPTION OF DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

DETAILED DESCRIPTION

Hereinafter, the present invention will be described in more detail to facilitate understanding of the present invention.

It will be understood that words or terms used in the description and claims of the present invention shall not be construed as being limited to having the meaning defined in commonly used dictionaries. It will be further understood that the words or terms should be interpreted as having meanings that are consistent with their meanings in the context of the relevant art and the technical idea of the invention, based on the principle that an inventor may properly define the meaning of the words or terms to best explain the invention.

The term "unpurified reaction product" according to the present specification may be a crude reaction product immediately after a reaction is performed in a reactor, and may specifically mean a reaction product on which an extraction process through steam is not performed.

The term "rich" according to the present specification means a component which accounts for 50 wt % or more when there are 2 components in a fraction, or a component which accounts for the largest amount when there are 3 or more components therein.

An "upper portion" of equipment described in the present specification, the equipment being, for example, a column, a distiller, a neutralizer, a wastewater treatment tank, or the like, may include, unless specifically specified, the top surface of each piece of equipment, thereby including a side top surface located above the center in the height direction of a side surface, and an "lower portion" of the equipment may include, unless specifically specified, the bottom surface of each piece of the equipment, thereby including a side bottom surface located below the center in the height direction of the side surface.

System for Continuous Purification

Figure 1:
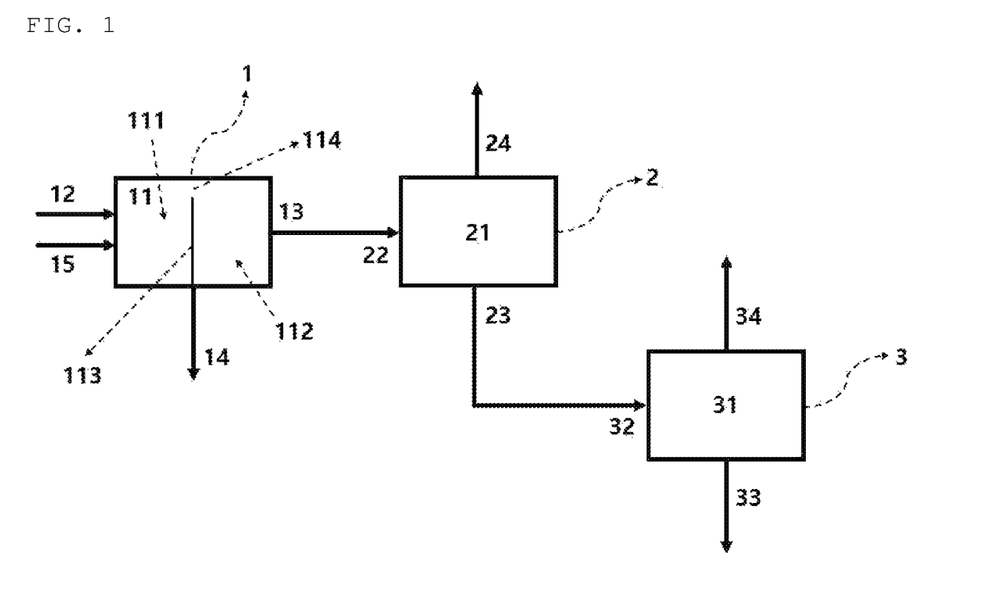
FIG. 1 is a process flow diagram illustrating a continuous purification system provided with a neutralizer, a distiller, and a product purifier according to an embodiment of the present invention.

A continuous purification system according to an embodiment of the present invention includes a neutralizer 1 including an inlet 12 into which an unpurified product mixture is injected, a neutralization agent injection port 15 through which a basic aqueous solution is injected, an inner space 11 in which neutralization and water separation are performed, a first discharge port 13 from which an organic layer fraction is discharged, and a second discharge port 14 from which a water layer fraction is discharged; a distiller including an organic layer fraction injection port 22 connected to the first discharge port 13 of the neutralizer, a separation space 21 in which the separation of the alcohol mixture is performed, an alcohol-rich stream discharge port 24 provided on an upper portion of the separation space 21, and an ester-rich stream discharge port 23 provided on a lower portion of the separation space; and a product purifier 3 including a purifier inlet 32 connected to the ester-rich stream discharge port 23 of the distiller, a purification space 31 in which gas-liquid separation is performed, an alcohol discharge port 34 provided on an upper portion of the purification space and from which an alcohol fraction is discharged, and a product discharge port 33 provided on a lower portion of the purification space and from which an ester fraction is discharged.

In addition, the inner space 11 of the neutralizer is provided with one or more partition walls 113 such that the inner space is divided into a neutralization space 111 and a layer separation space 112 in the left and right directions respectively and a passage 114 connecting the two spaces is formed, and the passage 114 starts from an upper portion of the neutralization space 111.

Referring to FIG. 1, in the continuous purification system according to an embodiment of the present invention, an unpurified product mixture is separated into an organic layer and a water layer in the neutralizer 1 having the inner space 11 divided into left and right by the one or more partition walls 113, wherein the neutralization space 111 is on the left and the layer separation space 112 is on the right, and including the inlet 12 and the neutralization agent injection port 15 provided on the side of the neutralization space 111, the first discharge port 13 provided on the upper side of the layer separation space 112, and the second discharge port 14 provided on the lower side of the layer separation space 112.

The organic layer fraction separated in the neutralizer 1 is connected to the distiller 2 through the first discharge port 13, and specifically, is connected to the organic layer fraction injection port 22 of the distiller 2. The distiller 2 is provided with the separation space 21 therein in which alcohol separation, such as reduced pressure extraction and steam extraction, is performed, and the alcohol-rich stream discharge port 24 is provided on an upper portion of the separation space and the ester-rich stream discharge port 23 is provided on a lower portion thereof. The distiller 2 may serve to control the loading amount of the product purifier 3 to be disposed at the rear end while reducing the content of alcohol in the organic layer fraction through the extraction of the alcohol.

An ester-rich stream is discharged from a lower portion of the distiller 2 through the ester-rich stream discharge port 23, which is connected to the purifier inlet 32 of the product purifier 3, and the ester-rich stream is injected into the purification space 31. In the purification space, gas-liquid separation may be performed as azeotropic distillation, that is, a distillation process through steam, and as a result, alcohols contained in the ester-rich stream are discharged from the alcohol discharge port 34 provided on an upper portion of the purification space and ester to be commercialized is discharged from the product discharge port 33 provided on the lower portion thereof.

The continuous purification system according to the present invention may further include a filter.

Figure 2:
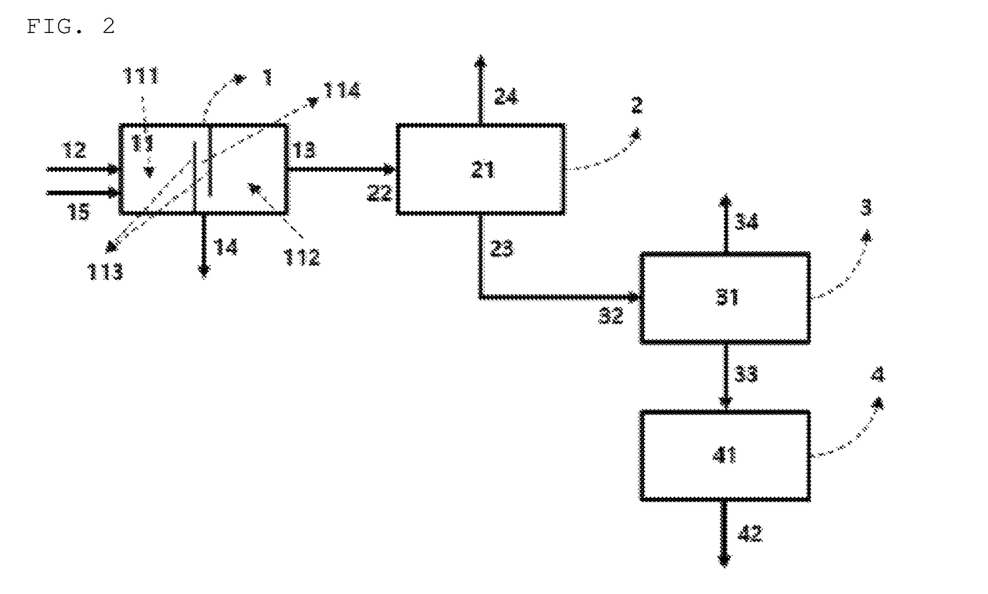
FIG. 2 is a process flow diagram illustrating a continuous purification system provided with a neutralizer, a distiller, a product purifier, and a filter according to an embodiment of the present invention.
Figure 3:
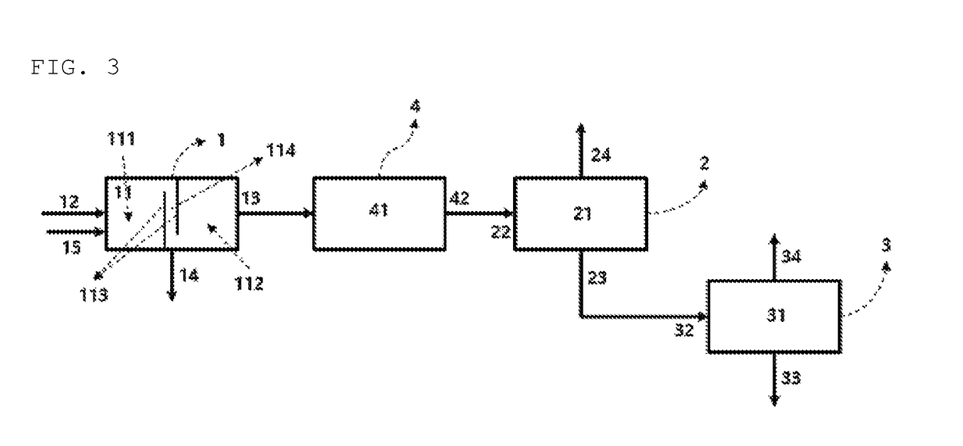
FIG. 3 is a process flow diagram illustrating a continuous purification system provided with a filter, a neutralizer, a distiller, and a product purifier according to an embodiment of the present invention.

Referring to FIG. 2 and FIG. 3, a filter 4 is connected to the product discharge port 33 of the product purifier 3 as shown in FIG. 2 to perform filtering in a filtering space 41, and a final product may be discharged through a filtered material discharge line 42. In addition, the filter 4 may be disposed before a purification process is performed, and as shown in FIG. 3, the filter 4 may be disposed at the rear end of the neutralizer 1 to allow the organic layer fraction is filtered first. In this case, the organic layer fraction injection port 22 may be connected to the filter 4, or the filtered material discharge line 42 may be connected to the distiller 2. However, it may be more preferable in terms of the quality of the final product that the filter is designed to be positioned at the rear end of the product purifier as shown in FIG. 2.

Figure 4:
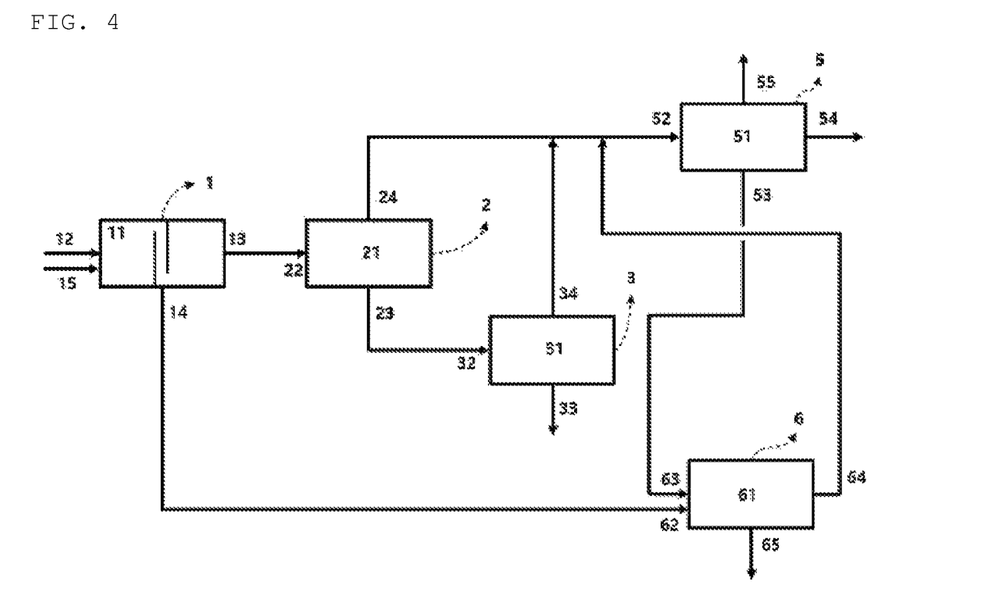
FIG. 4 is a process flow diagram illustrating a continuous purification system provided with a neutralizer, a distiller, a product purifier, a mixed alcohol separation column, and wastewater treatment tank according to an embodiment of the present invention.

According to an embodiment of the present invention, the system may further include a mixed alcohol separation column 5 including a mixed alcohol supply unit 52 in which the alcohol-rich stream discharge port 24 of the distiller 2 and the alcohol discharge port 34 of the product purifier 3 are connected, an upper removal unit 55 from which water is discharged, a middle discharge unit 54 from which lower alcohol is discharged, and a lower discharge unit 53 from which higher alcohol is discharged, and a wastewater treatment tank 6 including a lower alcohol wastewater line 62 connected to the second discharge port 14 of the neutralizer 1, a higher alcohol supply line 63 connected to the lower discharge unit 53 of the mixed alcohol separation column 5, a wastewater treatment space 61 in which mixing and layer separation are performed, an alcohol mixture discharge line 64 from which higher alcohol and lower alcohol are discharged, and a process wastewater treatment line 65.

The wastewater treatment space 61 of the wastewater treatment tank 6 is provided with one or more partition walls such that the wastewater treatment space is divided into a mixing space and a layer separation space in the left and right directions respectively and a passage connecting the two spaces is formed, wherein the passage may start from an upper portion of the mixing space. The alcohol mixture discharge line 64 of the wastewater treatment tank may be connected to the mixed alcohol supply unit 52 of the mixed alcohol separation column 5.

Referring to FIG. 4, the wastewater treatment tank 6 and the mixed alcohol separation column 5 may be further disposed. In the case of the mixed alcohol separation column 5, the alcohol-rich stream discharge port 24 discharged from the upper portion of the distiller 2 and the alcohol discharge port 34 of the product purifier 3 may be connected to the supply unit 52 of the mixed alcohol separation column 5. From the upper removal unit 55, water may be discharged. From the middle discharge unit 54, lower alcohol may be discharged, and from the lower discharge unit 53, higher alcohol may be discharged. Furthermore, in the alcohol separation space 51, the separation of water, lower alcohol, and higher alcohol is performed, which will be described later.

In addition, the wastewater treatment tank 6 may be a space in which the water layer fraction discharged from the second discharge port 14 of the neutralizer 1 is treated, and in the wastewater treatment tank, the second discharge port 14 of the neutralizer 1 may be connected to the lower alcohol wastewater line 62 of the wastewater treatment tank 6. The treatment of wastewater may be performed by higher alcohol separated from the mixed alcohol separation column 5, wherein the higher alcohol may be supplied through the higher alcohol supply line 63 through the lower discharge unit 53. In the wastewater treatment tank, higher alcohol and lower alcohol are separated into an organic layer by layer separation, and the mixed alcohol is discharged through the alcohol mixture discharge line 64, which may be connected to the supply unit of the mixed alcohol separation column. Wastewater containing substantially no alcohol or minimum alcohol may be discharged through the process wastewater treatment line 65 or may be recycled as process water.

Method for Continuous Purification

According to an embodiment of the present invention, there is provided a method for continuously purifying a reaction product of esterification, the method including a step S1 of performing layer separation on an unpurified product mixture including an alcohol mixture, as an unreacted material, containing two kinds of alcohol having different numbers of carbon atoms selected from 3 to 10 carbon atoms and including ester which is a product of an esterification reaction into an organic layer fraction which is rich in ester and a water layer fraction including lower alcohol in the presence of a basic aqueous solution in a neutralizer having a partition wall structure, a step S2 of injecting the organic layer fraction into a distiller to remove an alcohol-rich stream from an upper portion of the distiller and to discharge an ester-rich stream from a lower portion thereof, and a step S3 of injecting the ester-rich stream into a product purifier to separate an ester fraction from a lower portion of the product purifier and to separate an alcohol fraction from an upper portion thereof.

Typically, purification is performed by performing de-alcoholization, neutralization/water washing, and product separation in a non-continuous manner in a reactor after a reaction is performed in the reactor, or by performing each process in a respective apparatus in a non-continuous manner. In the case of a continuous process, as a means of a temporary solution, a piece of equipment such as a buffer tank is typically introduced at the front end of a column in which separation is continuously performed to control the loading amount of the column and to impart continuity. However, in the case of the purification method according to the present invention, a partition wall is provided in a neutralizer to function as a buffer tank at the same time, and neutralization and water separation are simultaneously performed by crossing the partition wall in an overflow manner in the neutralizer, so that there is an advantage in that an organic fraction is continuously supplied to a column.

The continuous purification method according to an embodiment of the present invention may be performed on an unpurified reaction product including ester in an amount of 50-95 parts by weight and an alcohol mixture in an amount of 5-50 parts by weight. As defined in the definition of the term, the unpurified reaction product may be a product included in a stream coming straight from a reactor, or a product in a state in which alcohol is not separately removed through steam extraction.

However, the present invention does not exclude filtering by a filter or stream exchange for heat exchange between a reactor and the neutralizer, and does not exclude a process of passing through equipment such as a reboiler, a condenser, or a pump on a process design.

Reaction Raw Materials and Esterification Reaction

The continuous purification method according to one embodiment of the present invention is a method for purifying a product of an esterification reaction, wherein the esterification reaction may be a trans-esterification reaction of reacting ester and alcohol.

The ester refers to a compound which has one or more ester group, and may be, for example, carboxylate-based compound, dicarboxylate-based compound, tricarboxylate-based compound or tetracarboxylate-based compound. Additionally, in case of dicarboxylate-based compound, the ester may be selected from group consisting of terephthalate, isophthalate, phthalate, cyclohexane 1,2-diester, cyclohexane 1,3-diester, and cyclohexane 1,4-diester, and in case of tricarboxylate-based compound, the ester may be selected from the group consisting of citrate, trimellitate and cyclohexane tricarboxylate-based compound, and in case of tetracarboxylate-based compound, the ester may be selected from the group consisting of benzene tetracarboxylate-based compound, furan tetracarboxylate-based compound, cyclohexane tetracarboxylate-based compound and tetrahydrofuran tetracarboxylated-based compound.

The ester may be a mixture of two or more ester compounds, and "a mixture of two or more ester compounds" refers to that two or more esters of same or different kind are comprised, but in a respect that one kind of a reaction product of esterification is purified, it is preferable that two or more esters of same kind are comprised.

In addition, the alcohol may be a mixture of two kinds of alcohols having different numbers of carbon atoms, and the number of carbon atoms may be 3 to 10. Alcohol having a smaller number of carbon atoms of the two alcohols may be referred to as lower alcohol, and alcohol having a larger number of carbon atoms may be referred to as higher alcohol. Preferably, the higher alcohol may have 6 to 10 carbon atoms, and the lower alcohol may have 3 to 5 carbon atoms.

Here, the lower alcohol may be a reactant of a trans-esterification reaction or an unreacted material thereof, and the higher alcohol may be a reactant of a direct esterification reaction or an unreacted material thereof, the reaction in which ester, a reactant of the trans-esterification reaction, is prepared. In addition, the lower alcohol may be used in the direct esterification reaction in which the ester is prepared, and the higher alcohol may be used in the trans-esterification reaction, so that the reaction may be performed as opposed to the above case. However, regardless of how the reaction is performed, the unpurified product mixture may include both the lower alcohol and the higher alcohol.

As the specific reaction conditions (temperature, pressure, time, and the like) of the trans-esterification reaction and the direct ester reaction, reaction conditions commonly applied in the art may be applied. However, the present invention is not particularly limited thereto.

According to an embodiment of the present invention, the reactor in which the trans-esterification reaction is performed may be a continuous stirred tank reactor (CSTR) and/or a plug flow reactor (PFR). Preferably, the reaction may be performed in a plug flow reactor or in a facility in which a plug flow reactor and a continuous stirred tank reactor are sequentially installed.

Step S1: Neutralization Step

According to an embodiment of the present invention, the continuous purification method first performs the step S1 of performing layer separation on an unpurified product mixture including an alcohol mixture, as an unreacted material, containing two kinds of alcohol having different numbers of carbon atoms selected from 3 to 10 carbon atoms and including ester which is a product of an esterification reaction into an organic layer fraction which is rich in ester and a water layer fraction including a small amount of the alcohol mixture in the presence of a basic aqueous solution in a neutralizer having a partition wall structure.

Meanwhile, in a typical process for purifying a product of an esterification reaction, when the reaction is completed, neutralization is performed to preferentially deactivate a catalyst and after the neutralization, the distillation of alcohol is performed under reduced pressure in a reactor or a distillation device in which the esterification reaction has been performed. This is a method which has been commonly performed since there is an advantage of being highly efficient in separating an unreacted alcohol from an ester product. In addition, since the distillation is performed under reduced pressure after the neutralization due to the structure of a facility, it is common that water is removed together with an alcohol mixture from an upper portion of the facility.

As described above, when the water is mixed with the alcohol mixture, specifically lower alcohol, and then separated, the lower alcohol is highly soluble in water, so that it is difficult to separate the alcohol. Also, the lower alcohol accounts for more than about 3.0 wt % of the entire stream, and thus, may cause a problem of being classified as a serious level of wastewater, and significant amounts of costs and energy are required for the separation and the treatment thereof. In addition, in an effort to reduce the content of the lower alcohol in the wastewater, a de-alcoholization process may performed to distill unreacted alcohol under reduced pressure immediately after the reaction is completed.

Accordingly, in the continuous purification method according to the present invention, a neutralizer having a partition wall structure is introduced, and through the introduction of the neutralizer, a water separation process (layer separation) may be performed to a significant degree along with a neutralization process. When neutralization and water separation are performed through the neutralizer according to the present invention, the alcohol mixture may be sent to an organic layer rich in ester, and thus, the amount of alcohol, especially a lower alcohol, leaked to a water layer may be minimized.

That is, typically, water and alcohol should be separated in a state in which ester is not present. However, according to the present invention, layer separation is performed in a state in which ester is present, thereby inducing alcohol into the organic layer, so that there is an advantage of minimizing the amount of lower alcohol contained in water. In the water layer which has been subjected to layer separation as described above, lower alcohol may be included in an amount of 0.5-3.0 parts by weight based on 100 parts by weight of the mixed weight of water and the lower alcohol. Substantially, the lower alcohol may be 2.0 parts by weight or less, even more substantially 1.0 parts by weight or less, and the content of lower alcohol in the wastewater may be reduced compared to a typical process.

Meanwhile, in a continuous purification process according to the present invention, the unpurified product mixture may include 50-95 parts by weight of ester and 5-50 parts by weight of alcohol, and since a step of removing unreacted material is not performed, the content of an alcohol component may be somewhat greater than that of ester, which is a product.

Neutralizer

According to an embodiment of the present invention, since the neutralizer has a partition wall structure, a purification process may be operated continuously. The structural properties of the partition wall structure are not particularly limited. However, one or more partition walls should be installed such that the space inside the neutralizer is separated into at least two spaces and a passage for connecting the two spaces is provided. For example, the neutralizer may have the same structure as that described above with reference to the continuous purification system.

In addition, an exit stream (organic layer fraction discharge port) of the neutralizer through which the organic layer fraction flows and an entrance stream (injection port) of the neutralizer through which the unpurified product mixture flows may be where mutual heat exchange is achieved. The unpurified product mixture which has been subjected to the trans-esterification reaction needs cooling since the unpurified product mixture is introduced while being at a high temperature due to the reaction of a high temperature and the organic layer fraction to be injected into a distillation column to be described later needs heating for distillation, energy consumption may be reduced by utilizing unnecessary heat of the entrance stream of the neutralizer as heat required for the exit stream thereof.

According to an embodiment of the present invention, in the neutralizer, the neutralization of the unpurified reaction product produced by the esterification reaction is performed, and a neutralization agent may be a basic aqueous solution having a base concentration of 0.1-50 wt %, and may be, for example, a sodium hydroxide aqueous solution or a sodium hydrogen carbonate aqueous solution. A basic aqueous solution having the base concentration as described above may be applied as the neutralization agent, and the neutralization of a catalyst and the neutralization of a reaction product may be performed using the same. Accordingly, a salt generated from the neutralization may be discharged through a waste liquid treatment port.

The unpurified product mixture may be injected into a neutralizer and added with a basic aqueous solution, which is a neutralization agent, to neutralize both a catalyst and a reaction product, and may be separated into an organic layer fraction and a water layer fraction, wherein the organic layer fraction may be rich in ester but contain alcohol and the water layer fraction may contain a small amount of alcohol and a trace of ester.

Here, the organic layer fraction may include 50-95 parts by weight of ester and 5-50 parts by weight of alcohol, and most of the alcohol may be separated during neutralization and water separation processes. Only a portion of lower alcohol, which is a portion of the alcohol, may be introduced into the water layer. Meanwhile, the content of the lower alcohol included in the water layer has been described above, and thus, the description thereof will be omitted.

In addition, a neutralization space and a layer separation space separated due to a partition wall of the neutralization unit and a passage are formed, so that the unpurified product mixture introduced is neutralized with a basic aqueous solution to form a salt in the neutralization space, and a predetermined amount is moved through the passage in an overthrow manner to the layer separation space to induce layer separation. As the layer separation is achieved in the layer separation space, the liquid surface of the organic layer continuously raises so that the organic layer fraction may be discharged from an upper end of the layer separation space and the water layer fraction containing the salt and the lower alcohol may be discharged through the waste liquid treatment port provided on a lower portion of the layer separation space.

The neutralization and water separation performed in the neutralizer may be performed in a range of about 30-150° C., and the capacity of the neutralizer may be about 5-300 m3. As other features not described in this specification, those applied in the art may be applied without being specifically limited.

Step S2: Alcohol Removal Step

According to an embodiment of the present invention, the continuous purification method performs the step S2 of injecting the organic layer fraction into a distiller to remove an alcohol-rich stream from an upper portion of the distiller and to discharge an ester-rich stream from a lower portion thereof.

The continuous purification method according to the present invention performs the step S2 to remove the alcohol present in the organic layer fraction, and the step S2 may be, in particular, a step in which most of the lower alcohol is removed.

A column may be applied to the distiller. However, reduced pressure distillation may be applied in equipment in the form of a drum, and any equipment capable of removing alcohol, mainly lower alcohol, may be applied without particular limitation. Also, when a column is installed, a buffer tank may be installed at the front end thereof as additional equipment. However, a piece of equipment such as a flash drum in the form of a drum may be preferably installed to function to control the loading amount of a product purifier at the rear end.

That is, in the step S2 according to an embodiment of the present invention, the organic layer fraction may include ester, lower alcohol, and higher alcohol, and when alcohol is removed in the distiller, there is an advantage in that only lower alcohol having the lowest boiling point is easily separated with only a small amount of energy, and at the same time, the loading amount of the product purifier at the rear end may be controlled.

At this time, the alcohol-rich stream separated from the upper portion of the distillation unit may include 50-100 parts by weight of lower alcohol and 0-50 parts by weight of higher alcohol based on 100 parts by weight of all materials in the alcohol-rich stream, and the ester-rich stream separated from the lower portion thereof may include 50-99 parts by weight of ester and 1-50 parts by weight of higher alcohol based on 100 parts by weight of all materials in the ester-rich stream.

The distiller may have a capacity of about 1-300 m3, may perform separation at about 30-200° C., and may be applied to pressure conditions of from normal pressure to a reduced pressure level of 10 mmHg. This range is a level which allows a refining process to be performed normally and efficiently, and if the above range is satisfied, refining may be efficiently performed.

Wastewater Treatment Tank

According to an embodiment of the present invention, the water layer fraction separated from the neutralizer may be sent to a wastewater treatment tank and be treated as wastewater. The water layer fraction of the neutralizer is injected into the wastewater treatment tank, and at this time, the higher alcohol separated (separated from a mixed alcohol column below) in a purification process may be used for wastewater treatment. That is, layer separation into an alcohol layer including higher alcohol and lower alcohol and a wastewater layer may be performed through an additional injection of the higher alcohol.

The wastewater treatment tank may have substantially the same structure as the above-described neutralizer, and may be in which the higher alcohol is injected together with the water layer fraction so that organic/water separation may be performed. When waster, the higher alcohol, and the lower alcohol are separated into an organic layer and a water layer, the organic layer may include an alcohol mixture and the water layer may include the lower alcohol in an amount of 0.01-3.0 wt % or less based on the total weight of the wastewater layer, and may include a process wastewater substantially having no lower alcohol.

Typically, neutralization is performed after the completion of a reaction and an alcohol mixture is separated with water by distillation. The separated stream is then injected into the alcohol separation column below and subjected to separation, thereby containing a significant amount of water, so that there has been problems in that column separation efficiency is extremely low and a considerable amount of energy is consumed for the separation. However, when the layer separation is performed through the wastewater treatment tank according to the present invention, there is an advantage in that lower alcohol in the wastewater may be easily separated without energy consumption.

Mixed Alcohol Column

The continuous purification method according to an embodiment of the present invention may perform a transesterification reaction as a reaction in which two or more alcohols are included, and accordingly separation and recovery of used or unreacted alcohol may have a significant impact on purification efficiency. For example, when both lower alcohol and higher alcohol are used in the transesterification reaction, moisture generated in the process (such as an upper stream of a product purifier) may be included with the alcohol so that three phases are azeotropic, and there may be problems of, such as, requiring a significant number of column stages or introducing several pieces of distillation column equipment.

However, the continuous purification method according to an embodiment of the present invention introduces a mixed alcohol column together with s a mixed alcohol tank for buffering the loading amount of alcohol, so that the separation of the three-phase mixture of water, lower alcohol, and higher alcohol may be facilitated.

To the mixed alcohol column, the alcohol-rich stream separated from the upper portion of the above-described distiller, the alcohol fraction separated from the upper portion of the above-described product purifier, and the alcohol layer of the wastewater treatment tank may be introduced.

In the mixed alcohol column, water, higher alcohol, and lower alcohol may be separated, and the water may be removed from the upper end of the column, the lower alcohol may be discharged and recovered through a discharge port provided on the middle end side surface portion of the column and recycled in the reaction, and the higher alcohol may be discharged from a discharge port positioned at the lowermost end of the column. The higher alcohol may also be recycled in the process, wherein a portion thereof may be injected into the wastewater treatment tank described above to recover the lower alcohol included in the wastewater, and then recovered in the mixed alcohol tank together with the lower alcohol.

Step S3: Ester Obtaining Step in Product Purifier

According to an embodiment of the present invention, the continuous purification method performs the step S3 of injecting the ester-rich stream into a product purifier to separate an ester fraction from a lower portion of the product purifier and to separate an alcohol fraction from an upper portion thereof.

In the step S3, the product purifier may be used to separate a final product, and in the product purifier, alcohol remaining in the organic layer fraction from which the lower alcohol is removed may be separated from an upper portion of the product purifier and ester to be commercialized may be separated from a lower portion therefrom. Distillation using steam may also be performed in the purifier, and the purifier may be in the form of a column or in the form of a drum, but may be preferably a column.

The product purifier may have a capacity of about 10-300 m3, may perform at 30-200° C., and may be applied to pressure conditions of from normal pressure to a reduced pressure level of 10 mmHg. This range is a level which allows a refining process to be performed normally and efficiently, and if the above range is satisfied, refining may be efficiently performed.

The ester fraction separated from the product purifier is commercialized, and the alcohol fraction separated from the upper portion thereof is transferred to the mixed alcohol tank so that three phase separation may be performed in the mixed alcohol column.

Filtering Step

According to an embodiment of the present invention, the continuous purification method may further include a step of filtering through a filter.

The step of filtering may be either performed on an unpurified product mixture before the step S1, or performed on the ester fraction which is a product separated through a lower portion after the step S3. That is, the filter may be installed at the front end of the neutralizer and may be installed at the rear end of the separation column lower stream which is a final product column. Any method known in the art may be applied to the filtering without particular limitation, and the filtering may be performed using filters of various materials, and the like.

EXAMPLES

The residual alcohol content in wastewater generated when using a typical batch purification process and the residual alcohol content in wastewater generated when using the continuous purification process of the present invention were compared. In the typical batch purification process, an unpurified product mixture was all transferred to a neutralizer of the prior art not having a partition wall, and then an appropriate amount of a basic aqueous solution was added as a neutralization agent thereto. Then, the mixture was stirred to complete neutralization. Thereafter, the neutralized unpurified product mixture was all transferred to a separate layer separation apparatus to separate a water layer, and then transferred to another separate wastewater treatment tank to treat higher alcohol, thereby obtaining wastewater having a reduced amount of residual alcohol.

The unpurified product mixtures used in the purification processes were identical to each other and included butanol. Finally, the content of butanol remaining in the wastewater obtained in each of the processes was compared to compare the purification effect in each purification process. The butanol content in the wastewater was measured using gas chromatography (G.C.). In addition, the wastewater obtained in each process was treated with various amounts of 2-ethylhexanol to determine how much content of butanol in wastewater may be reduced.

Specifically, 2-ethylhexanol in an appropriate amount was added to 60 g of wastewater and the mixture was stirred for 30 minutes, followed by being left to stand for 30 minutes. Thereafter, a wastewater layer was separated therefrom to confirm the content of residual butanol by gas chromatography. The content of butanol in the wastewater with respect to the injection amount of 2-ethylhexanol was illustrated in a graph and shown in FIG. 5.

Figure 5:
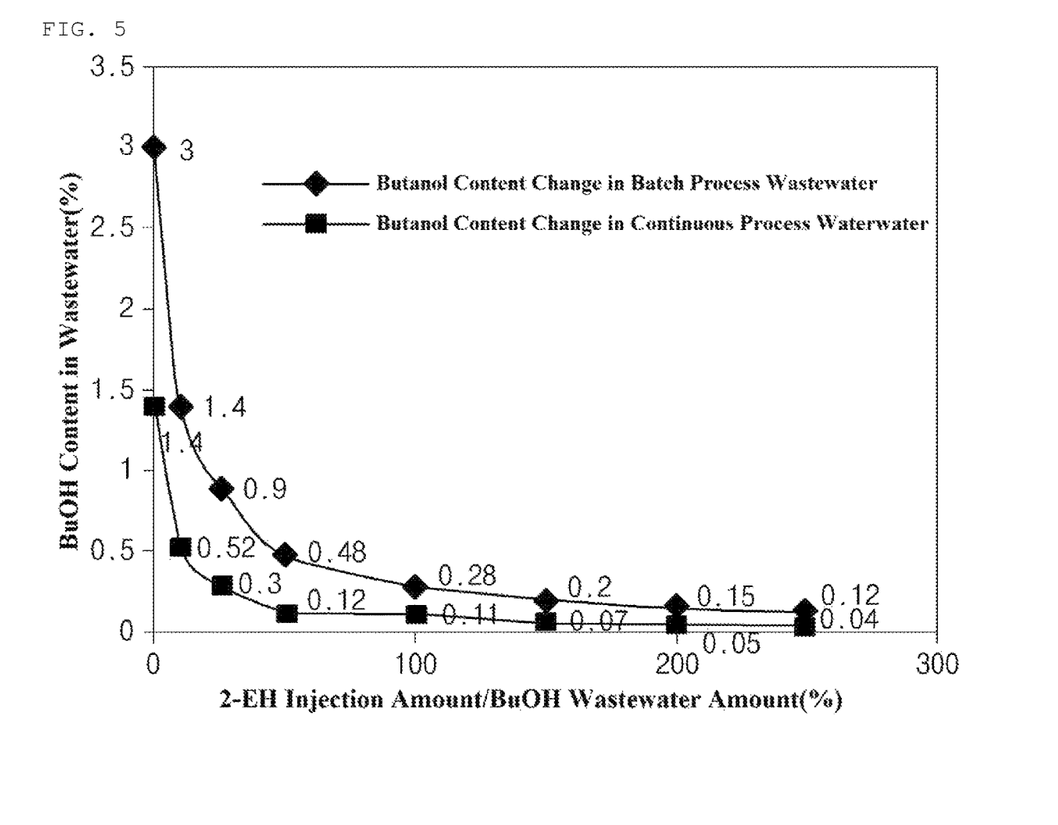
FIG. 5 is a graph showing the amount of alcohol in wastewater in a typical batch process and a continuous process of the present invention.

As shown in FIG. 5, the wastewater obtained in the batch purification process showed a butanol content of 3%, whereas the wastewater obtained in the continuous purification process of the present invention showed a butanol content of 1.4%, so that it was confirmed that the alcohol content in the wastewater was equal to or less than half compared to that of the typical batch purification process. In addition, for all the cases in which the wastewater was treated with 2-ethylhexanol to remove butanol from the wastewater, it was confirmed that the butanol content in the wastewater of the continuous purification process of the present invention was lower than that of the typical batch purification process.

DESCRIPTION OF THE REFERENCE NUMERALS OR SYMBOLS

1: Neutralizer
11: Inner space
12: Inlet
13: First discharge port
14: Second discharge port
15: Neutralization agent injection port
2: Distiller
21: Separation space
22: Organic layer fraction injection port
23: Ester-rich stream discharge port
24: Alcohol-rich stream discharge port
3: Product purifier
31: Purification space
32: Purifier inlet
33: Product discharge port
34: Alcohol discharge port
4: Filter
42: Filtered material discharge line
5: Mixed alcohol separation column
51: Mixed alcohol separation space
52: Mixed alcohol supply unit
53: Lower discharge unit
54: Middle discharge unit
55: Upper remover unit
6: Wastewater treatment tank
61: Wastewater treatment space
62: Alcohol wastewater line
63: Higher alcohol supply line
64: Alcohol mixture discharge line
65: Process wastewater treatment line

The invention claimed is:

1. A system for continuously purifying a reaction product of esterification, the system comprising:
a neutralizer including an inlet into which an unpurified product mixture containing a mixture of two kinds of alcohols having different esters and different numbers of carbon atoms is injected, a neutralization agent injection port through which a basic aqueous solution is injected as a neutralization agent, an inner space in which neutralization and water separation are performed, a first discharge port from which an organic layer fraction is discharged, and a second discharge port from which a water layer fraction is discharged;
a distiller including an organic layer fraction injection port connected to the first discharge port of the neutralizer, a separation space in which the separation of the alcohol mixture is performed, an alcohol-rich stream discharge port provided on an upper portion of the separation space, and an ester-rich stream discharge port provided on a lower portion of the separation space; and
a product purifier including a purifier inlet connected to the ester-rich stream discharge port of the distiller, a purification space in which gas-liquid separation is performed, an alcohol discharge port provided on an upper portion of the purification space and from which an alcohol fraction is discharged, and a product discharge port provided on a lower portion of the purification space and from which an ester fraction is discharged,
wherein the inner space of the neutralizer is provided with one or more partition walls such that the inner space is divided into a neutralization space and a layer separation space in the left and right directions respectively and a passage connecting the two spaces is formed, and the passage starts from an upper portion of the neutralization space.

2. The system of claim 1, wherein the neutralizer further comprises a neutralization agent injection port through which a basic aqueous solution is injected into the neutralization space and a waste liquid treatment port from which a waste liquid is discharged from the layer separation space.

3. The system of claim 1, further comprising
a mixed alcohol separation column including a mixed alcohol supply unit in which the alcohol-rich stream discharge port of the distiller and the alcohol discharge port of the product purifier are connected, an upper removal unit from which water is discharged, a middle discharge unit from which lower alcohol is discharged, and a lower discharge unit from which higher alcohol is discharged; and
a wastewater treatment tank including a lower alcohol wastewater line connected to the second discharge port of the neutralizer, a higher alcohol supply line connected to the lower discharge unit of the mixed alcohol separation column, a wastewater treatment space in which mixing and layer separation are performed, an alcohol mixture discharge line from which higher alcohol and lower alcohol are discharged, and a process wastewater treatment line, wherein the wastewater treatment space of the wastewater treatment tank is provided with one or more partition walls such that the wastewater treatment space is divided into a mixing space and a layer separation space in the left and right directions respectively and a passage connecting the two spaces is formed, and the passage starts from an upper portion of the mixing space.

4. A method for continuously purifying a reaction product of esterification, the method comprising:
a step S1 of performing layer separation on an unpurified product mixture including an alcohol mixture, as an unreacted material, containing two kinds of alcohols having different numbers of carbon atoms selected from 3 to 10 and including ester which is a product of an esterification reaction into an organic layer fraction which is rich in ester and a water layer fraction including lower alcohol in the presence of a basic aqueous solution in a neutralizer having a partition wall structure;
a step S2 of injecting the organic layer fraction into a distiller to remove an alcohol-rich stream from an upper portion of the distiller and to discharge an ester-rich stream from a lower portion thereof; and
a step S3 of injecting the ester-rich stream into a product purifier to separate an ester fraction from a lower portion of the product purifier and to separate an alcohol fraction from an upper portion thereof.

5. The method of claim 4, wherein the water layer fraction comprises water and lower alcohol, and the lower alcohol of the water layer fraction is included in an amount of 0.5-3.0 parts by weight based on 100 parts by weight of the mixed weight of the water and the lower alcohol.

6. The method of claim 4, wherein both a neutralization of a catalyst and a neutralization of the unpurified product mixture are performed in the neutralizer.

7. The method of claim 4, wherein mutual heat exchange is performed between an exit stream of the neutralizer through which the organic layer fraction flows and an entrance stream of the neutralizer through which the unpurified product mixture flows.

8. The method of claim 4, wherein the basic aqueous solution injected into the neutralizer has a base concentration of 0.1-50 wt %.

9. The method of claim 4, wherein in the product purifier of the step S3, separation by distillation using steam is performed.

10. The method of claim 4, further comprising a step of filtering using a filer, wherein the step of filtering is either performed on an unpurified product mixture before the step S1, or performed on the ester fraction which is a product separated through a lower portion of the product purifier after the step S3.

11. The method of claim 4, wherein the water layer fraction is injected into a wastewater treatment tank and through the injection of higher alcohol, subjected to layer separation into an alcohol layer including the higher alcohol and the lower alcohol, and a wastewater layer.

12. The method of claim 11, wherein the alcohol-rich stream separated from the upper portion of the distiller and the alcohol fraction separated from the upper portion of the product purifier, and the alcohol layer of the wastewater treatment tank are injected into a mixed alcohol separation column to separate higher alcohol and lower alcohol.

13. The method of claim 11, wherein the wastewater layer contains the lower alcohol in an amount of 3.0 wt % or less based on the total weight of the wastewater layer.

14. The method of claim 4, wherein the ester is one or more selected from the group consisting of terephthalate, isophthalate, phthalate, cyclohexane 1,2-diester, cyclohexane 1,3-diester, cyclohexane 1,4-diester, citrate, trimellitate, cyclohexane tricarboxylate-based compound, benzene tetracarboxylate-based compound, furan tetracarboxylate-based compound, cyclohexane tetracarboxylate-based compound and tetrahydrofuran tetracarboxylate-based compound.

\* \* \* \* \*